United States Patent
Hohlrieder et al.

(10) Patent No.: US 11,197,748 B2
(45) Date of Patent: Dec. 14, 2021

(54) MEDICAL DEVICE FOR NARROWING OR CLOSING AN ANATOMICAL CHANNEL

(71) Applicant: A.M.I. Agency for Medical Innovations GmbH, Feldkirch (AT)

(72) Inventors: Martin Hohlrieder, Gotzis (AT); Thomas Gillen, Bad Sackingen (DE)

(73) Assignee: A.M.I. Agency for Medical Innovations GmbH, Feldkirch (AT)

( * ) Notice: Subject to any disclaimer, the term of this patent is extended or adjusted under 35 U.S.C. 154(b) by 329 days.

(21) Appl. No.: 16/097,700

(22) PCT Filed: May 29, 2017

(86) PCT No.: PCT/AT2017/000042
§ 371 (c)(1),
(2) Date: Oct. 30, 2018

(87) PCT Pub. No.: WO2017/205883
PCT Pub. Date: Dec. 7, 2017

(65) Prior Publication Data
US 2019/0133737 A1    May 9, 2019

(30) Foreign Application Priority Data

Jun. 3, 2016    (AT) .................................. A 274/2016

(51) Int. Cl.
| A61F 2/00 | (2006.01) |
| A61F 5/00 | (2006.01) |
| A61F 2/04 | (2013.01) |

(52) U.S. Cl.
CPC .............. *A61F 2/004* (2013.01); *A61F 5/003* (2013.01); *A61F 5/0059* (2013.01);
(Continued)

(58) Field of Classification Search
CPC .............. A61F 2250/0002; A61F 2/004; A61F 5/0059; A61F 2005/002; A61F 5/003;
(Continued)

(56) References Cited

U.S. PATENT DOCUMENTS

| 3,863,622 A | 2/1975 | Buuck |
| 4,222,377 A | 9/1980 | Burton |

(Continued)

FOREIGN PATENT DOCUMENTS

| CN | 101120895 | 2/2008 |
| CN | 101460218 | 6/2009 |

(Continued)

OTHER PUBLICATIONS

Artifical Urinary Sphincter, Wikipedia, 2 pages, downloaded on Apr. 19, 2016, https://en.wikipedia.org/wiki/Artificial_urinary_sphincter.

*Primary Examiner* — Navin Natnithithadha
*Assistant Examiner* — Sunita Reddy
(74) *Attorney, Agent, or Firm* — Volpe Koenig (57) ABSTRACT

A medical device for narrowing or closing an anatomical channel includes a band part (1) which can be placed around the body tissue (2) surrounding the anatomical channel and which can be closed to form a ring that encloses a through-opening (6) for the body tissue, wherein the band part (1) has a hollow chamber (3), and wherein the through-opening (6) can be made smaller by introducing a fluid into the hollow chamber (3). The medical device moreover includes a pump unit (10) which serves to convey the fluid and which has an electric drive (15) controllable by an electronic control system of the device, wherein a pressure value corresponding to the pressure of the fluid in the hollow chamber (3) or dependent on this pressure can be detected by the electronic (Continued)

control system. The device moreover has an air pressure sensor (23) for detecting the atmospheric pressure.

14 Claims, 4 Drawing Sheets

(52) U.S. Cl.
CPC ... *A61F 2002/041* (2013.01); *A61F 2005/002* (2013.01); *A61F 2220/0033* (2013.01); *A61F 2250/0001* (2013.01); *A61F 2250/0002* (2013.01); *A61F 2250/0009* (2013.01); *A61F 2250/0013* (2013.01)

(58) Field of Classification Search
CPC ...... A61F 2220/0033; A61F 2250/0001; A61F 2250/0013; A61F 2250/0009; A61F 2002/041
USPC ................................. 600/29–32, 37
See application file for complete search history.

(56) References Cited

U.S. PATENT DOCUMENTS

| | | | |
|---|---|---|---|
| 4,417,567 A | 11/1983 | Trick | |
| 4,721,509 A | 1/1988 | Craggs | |
| 4,784,660 A | 11/1988 | Fischell | |
| 5,478,305 A | 12/1995 | Craggs | |
| 5,478,405 A | 12/1995 | Craggs | |
| 5,976,109 A | 11/1999 | Heruth | |
| 6,461,292 B1* | 10/2002 | Forsell | A61F 2/0036 600/31 |
| 6,470,892 B1* | 10/2002 | Forsell | A61B 17/1322 128/899 |
| 6,475,136 B1* | 11/2002 | Forsell | A61F 2/0036 600/37 |
| 7,172,607 B2 | 2/2007 | Hofle et al. | |
| 7,217,237 B2 | 5/2007 | Wassermann et al. | |
| 8,870,742 B2 | 10/2014 | Dlugos et al. | |
| 10,139,304 B2 | 11/2018 | Lamraoui | |
| 2003/0045775 A1* | 3/2003 | Forsell | A61F 2/0018 600/31 |
| 2003/0105385 A1* | 6/2003 | Forsell | A61F 2/0036 600/29 |
| 2004/0260319 A1 | 12/2004 | Egle | |
| 2005/0240144 A1 | 10/2005 | Wassemann et al. | |
| 2006/0183967 A1 | 8/2006 | Lechner | |
| 2006/0211913 A1* | 9/2006 | Dlugos | A61F 2/004 600/37 |
| 2007/0156013 A1* | 7/2007 | Birk | A61B 5/036 600/37 |
| 2009/0248109 A1 | 10/2009 | Forsell | |
| 2010/0076254 A1 | 3/2010 | Jimenez et al. | |
| 2010/0211175 A1 | 8/2010 | Gomez-Llorens | |
| 2012/0123195 A1 | 5/2012 | Woodruff et al. | |
| 2012/0130157 A1 | 5/2012 | Cotner et al. | |
| 2012/0157759 A1 | 6/2012 | Wirbisky et al. | |
| 2014/0364686 A1 | 12/2014 | McClurg | |
| 2015/0359617 A1 | 12/2015 | Forsell | |
| 2016/0089224 A1* | 3/2016 | Taylor | A61F 2/004 600/31 |
| 2016/0123835 A1* | 5/2016 | Lamraoui | A61F 5/005 600/31 |
| 2017/0252141 A1* | 9/2017 | Alharmi | A61B 5/6874 |

FOREIGN PATENT DOCUMENTS

| | | |
|---|---|---|
| CN | 105393100 | 3/2016 |
| DE | 9308196 | 12/1993 |
| DE | 10013519 | 10/2001 |
| DE | 202007004083 | 8/2007 |
| EP | 0348114 | 12/1989 |
| EP | 1389453 | 2/2004 |
| EP | 1484038 | 8/2007 |
| EP | 1832253 | 9/2007 |
| EP | 1992315 | 11/2008 |
| EP | 2123238 | 11/2009 |
| EP | 2400239 | 12/2011 |
| FR | 1291158 | 3/1962 |
| FR | 2373272 | 7/1978 |
| WO | 2009136121 | 11/2009 |
| WO | 2009136124 | 11/2009 |
| WO | 2017214643 | 12/2017 |
| WO | 2017214644 | 12/2017 |

* cited by examiner

MEDICAL DEVICE FOR NARROWING OR CLOSING AN ANATOMICAL CHANNEL

BACKGROUND

The invention relates to a medical device for narrowing or shutting off an anatomical channel, said device comprising a band part which can be placed around the body tissue surrounding the anatomical channel and which can be closed to form a ring that encloses a through-opening for the body tissue, wherein the band part has a hollow chamber, and wherein the through-opening can be made smaller by introducing a fluid into the hollow chamber, and a pump unit which serves to convey the fluid and which has an electric drive controllable by an electronic control system of the device, wherein a pressure value corresponding to or dependent on the pressure of the fluid in the hollow chamber can be detected by the electronic control system.

Medical devices for narrowing or shutting off an anatomical channel are used, inter alia, as artificial (sphincter) muscles for aiding or replacing weakened natural muscles in the human or animal body. Examples of the uses of such devices are anal bands for closing an anus, possibly an artificial anus, and artificial sphincter muscles for closing the urethra in order to treat incontinence. Further areas of use are, for example, gastric bands for narrowing the gastrointestinal tract or bands for closing a bile duct. Medical devices of these kinds are also designated as cuffs or artificial sphincters.

The hollow chamber can be emptied by the user when necessary in order to increase the cross-sectional area of the through-opening and to allow substances and/or liquids contained in the anatomical channel to pass through. For example, in the use as an artificial sphincter muscle for the urethra, there is often a subsequent automatic closure of the anatomical channel by reverse pumping of fluid (optionally via a throttle valve) into the hollow chamber of the device. In an artificial urinary sphincter of this kind for male patients, a pump for pumping fluid is usually implanted in the scrotum. The pumping of fluid out of the hollow chamber can then be effected by pressure exerted on a flexible part of the pump. The reverse pumping of fluid into the hollow chamber can be effected by a resiliently elastic element of the pump. The through-opening of the medical device can often also be made smaller again by deliberate manipulation by the user, i.e. by manual actuation of the pump.

For example, U.S. Pat. No. 5,478,305 A discloses a medical device which is referred to as a cuff in said document and which can be used for treating urinary or fecal incontinence. The cuff is made of silicone. By filling the cuff with fluid, the pressure in the hollow space of the cuff rises and closes the anatomical channel. Examples of gastric bands are disclosed in EP 1 389 453 B1.

Moreover, implantable medical devices are known by which a liquid medicament can be delivered in doses to a desired location within the body. U.S. Pat. No. 5,976,109 A discloses such a device in which a container with a flexible wall, for example in the form of a bellows, is provided, wherein a cover part of the container for metering the medicament is adjusted by an electric drive. The container thus simultaneously forms a reservoir for the medicament and also a part of a pump by which the medicament is conveyed to the desired location in the body.

A device of the type mentioned at the outset is disclosed in DE 100 13 519 A1. This device is an implantable sphincter prosthesis for use in urinary incontinence. An electrically driven pump part serves to convey the fluid. Here, energy is supplied by an extracorporeal control and supply unit, from which the drive of the pump part can be supplied with electrical energy in a wireless manner. In the region of the band part, a pressure sensor is provided by which the pressure exerted on the urethra by the band part is determined. This pressure sensor can be used to calibrate the system, i.e. to set the closing pressure. When use is made of a pump with a reversible delivery direction or of a switching valve, the pressure sensor can also be utilized to set the delivery direction, i.e. from the sphincter prosthesis into a reservoir or vice versa.

EP 1 832 253 A1 discloses a gastric band with a pressure sensor for determining the fluid pressure in the gastric band. This document further discloses an air pressure sensor, from which the measured value is used to correct the fluid pressure value determined by the pressure sensor. In this way, the precision of the pressure measurement can be enhanced and a current pressure in the gastric band can be determined and output at a display unit. A person skilled in the art can then precisely adjust the pressure in the gastric band, wherein fluid can be delivered or withdrawn manually, e.g. by a syringe, via a port implanted in the body.

SUMMARY

The object of the invention is to make available a device which is of the type mentioned at the outset and which permits improved operation. This is achieved by a device having one or more features of the invention.

The device according to the invention has an air pressure sensor. The electronic control system is thus able to detect an air pressure value which is output by this air pressure sensor and which corresponds to the atmospheric pressure. In particular, using pressure values which are detected at different times and correspond to or depend on the respective pressure of the fluid in the hollow chamber, and using detected air pressure values which correspond to the respective atmospheric pressure, the control system is able to establish a change of the fluid volume in the system and can optionally adapt the pressure for the fluid and/or can output a warning if the established liquid volume goes beyond an upper or lower limit value.

Such a change of the liquid volume can be caused, for example, by osmosis or by a leak.

Optimal pressure conditions at the urethra can advantageously be achieved by the device according to the invention.

In one possible embodiment, a pressure value corresponding to the pressure of the fluid in the hollow chamber can be detected by a pressure sensor arranged in the fluid.

It is also conceivable and possible for a pressure sensor to be arranged on a surface of the band part delimiting the through-opening. A pressure value detected by such a pressure sensor depends at any rate on the pressure of the fluid in the hollow chamber and may preferably be at least substantially proportional to the pressure of the fluid in the hollow chamber.

A pressure value could also be measured by a strain gauge affixed to a membrane which deforms due to pressure fluctuations. The membrane delimits a space in which the fluid is located. For example, the membrane could also be formed from a portion of the band part itself. By use of such a membrane with an affixed strain gauge, a pressure sensor is formed which borders the fluid. A pressure value detected by a pressure sensor configured in this way is at any rate also dependent on the pressure of the fluid in the hollow chamber and may preferably be at least substantially proportional to the pressure of the fluid in the hollow chamber.

Depending on the electric drive used, a pressure value corresponding to or dependent on the pressure of the fluid in the hollow chamber could also be derived from the current consumption of the electric drive of the pump device.

In an advantageous embodiment, provision is made that the pump unit has a pump part having a receiving space which is filled with the fluid and of which the volume is variable by the drive. For example, the pump part can be a bellows closed by a bottom part and a cover part. It is also conceivable and possible for the pump part to be configured in the form of a piston-cylinder unit. The pressure sensor for detecting the pressure of the fluid in the hollow chamber of the band part can be arranged in such a receiving space of a pump part. An arrangement directly in the hollow chamber of the band part or in the channel of a hose connecting the band part to the pump part is also conceivable and possible.

The device preferably has an operating unit arranged spatially separate from the pump unit (and from the band part), which operating unit has at least one operating element that can be actuated by a user in order to open and/or shut off the anatomical channel. The operating unit advantageously has an operating electronics unit, which communicates with a pump electronics unit of the pump unit via a radio link. This operating unit can be provided outside the body. It is also conceivable and possible for the operating unit to be implanted, specifically in a manner independent of the site of implantation of the band part and of the pump unit.

The air pressure sensor can be arranged in the operating unit, which is either implanted or arranged outside the body. An arrangement of the air pressure sensor in the pump unit is also possible.

The device can be configured as an artificial urethral sphincter, for example. In other embodiments, the device according to the invention can be configured, for example, as an artificial anal sphincter, an artificial sphincter of Oddi, or an artificial occlusion of a bile duct.

The shutting-off of the anatomical channel can be a complete shutting-off or a partial shutting-off (narrowing).

BRIEF DESCRIPTION OF THE DRAWINGS

Further advantages and details of the invention are explained below with reference to the attached drawing, in which.

DETAILED DESCRIPTION

An illustrative embodiment of a device according to the invention is depicted in the figures.

A band part 1 of the device can be placed in a ring shape around the body tissue 2 surrounding the anatomical channel, here the urethra. The band part 1 has a hollow chamber 3 which extends in the direction of the longitudinal extent of the band part, in the illustrative embodiment substantially along the entire length of the band part. The band part 1 is thus configured like a hose, with ends closed at both sides.

A first and a second closure part 4, 5 are arranged at the two ends of the band part 1. The first closure part 4 has an insertion opening 4a into which a tongue 5a of the second closure part 5 can be inserted and locked therein.

Figure 3:
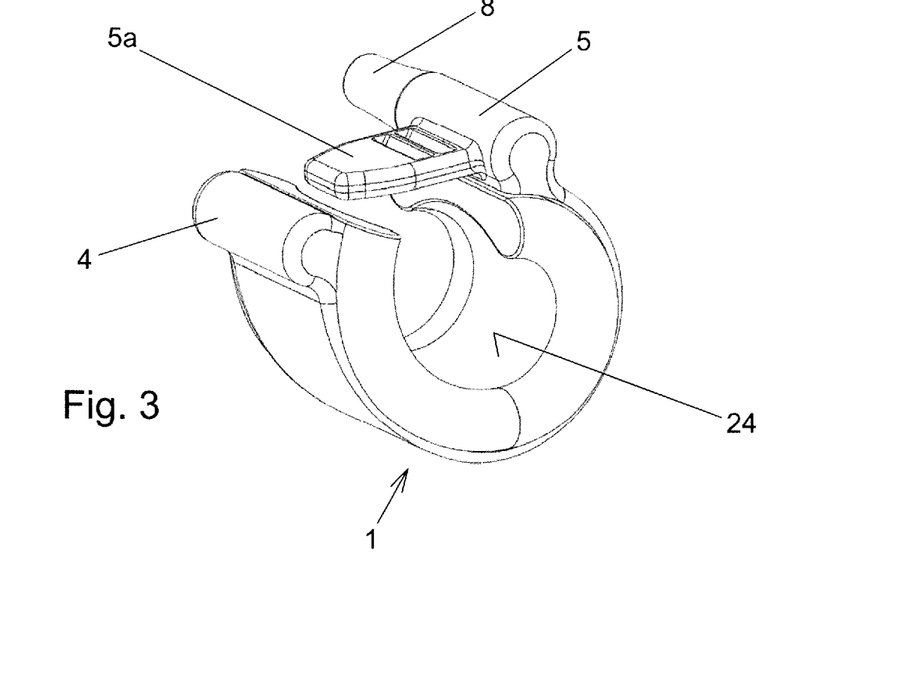
FIGS. 3 and 4 show perspective views of the free, i.e. not implanted, band part of the device in an opened state and a closed state, specifically corresponding to the release state.
Figure 4:
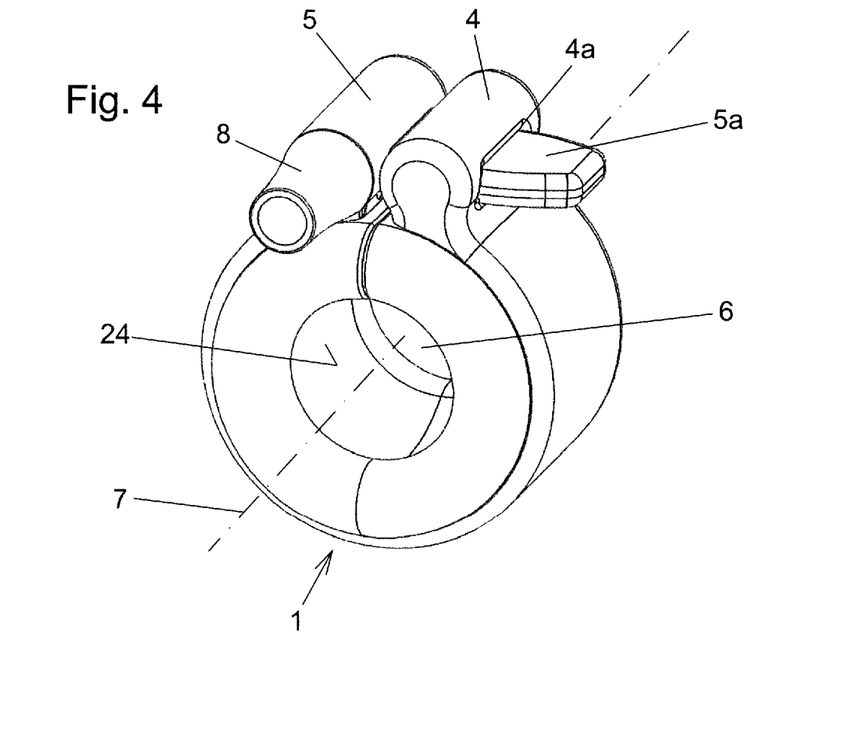

The closure parts 4, 5 thus form a closure with which the band part 1 can be closed to form a ring, in particular a circular ring (cf. FIG. 3). In the closed state, the band part 1 encloses a through-opening 6 for the body tissue 2 surrounding the anatomical channel.

A fluid, in particular a liquid, is located in the hollow chamber 3. The size of the through-opening 6 depends on the amount of the fluid in the hollow chamber 3. The through-opening 6 can be made smaller by introducing fluid into the hollow chamber 3. An inner flexible portion 1a of the band part 1, i.e. a portion adjacent to the longitudinal center axis 7 of the through-opening 6, is displaced in the direction of the longitudinal center axis 7, as is known. By removing fluid from the hollow chamber 3, the through-opening 6 can be made larger again.

Figure 5:
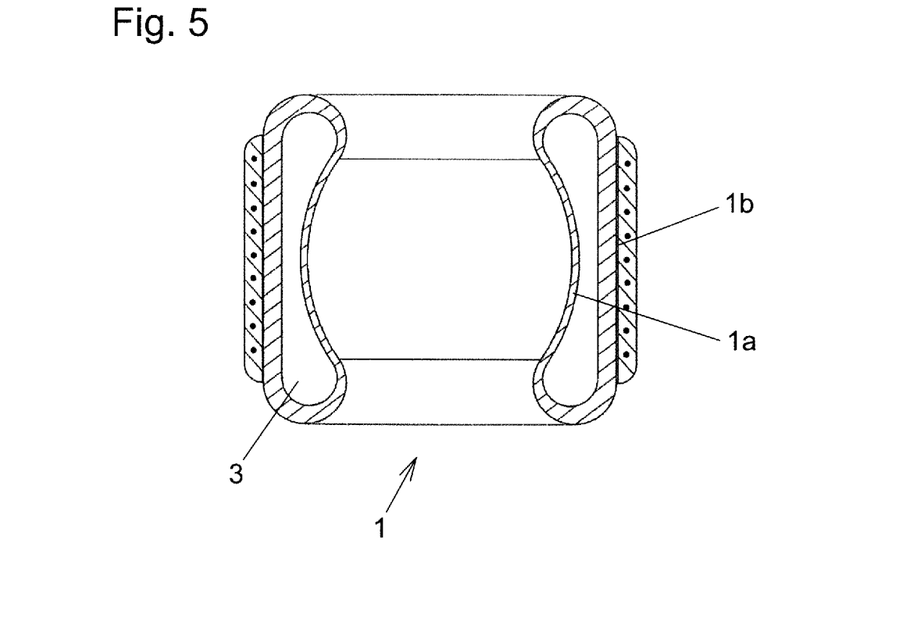
FIG. 5 shows a longitudinal center section (parallel to the longitudinal center axis of the through-opening and extending through the latter) through the band part in the state shown in FIG. 4.
Figure 6:
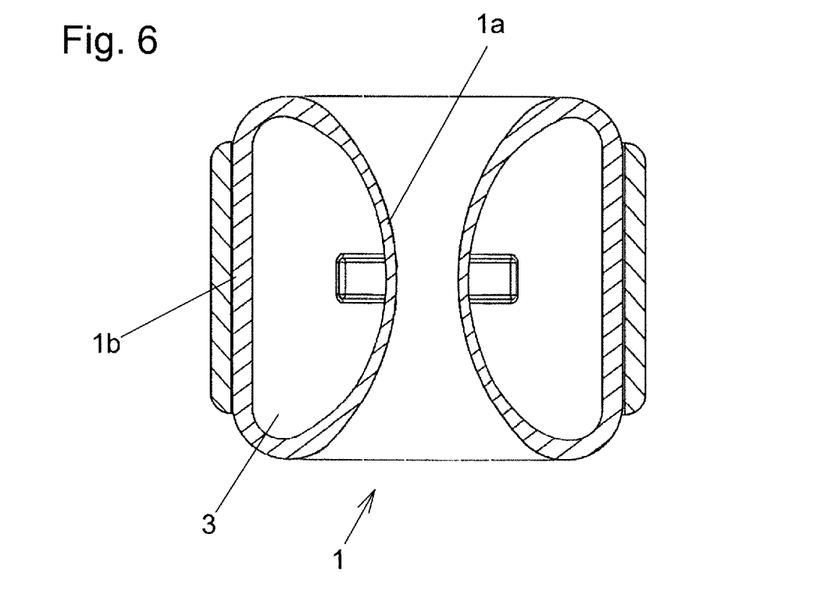
FIG. 6 shows a longitudinal center section analogous to FIG. 5, but in the shut-off state of the band part.

FIG. 5 shows the state in which the through-opening 6 is at its largest (wherein the pressure of the fluid in the hollow chamber 3 corresponds to the ambient pressure), while FIG. 6 shows a state in which it is filled with more fluid, in particular the state in which it is filled to the maximum with fluid (wherein the pressure of the fluid in the hollow chamber 3 is above the ambient pressure). The formation of folds, which would occur in particular if the band part is not placed around the ureter, are not shown in FIG. 6.

By contrast, a rear portion 1b of the band part 1, set back from the longitudinal center axis 7, can be made stiffer, in particular by a reinforcement layer, as a result of which a deformation of the rear portion can be at least largely avoided.

Figure 1:
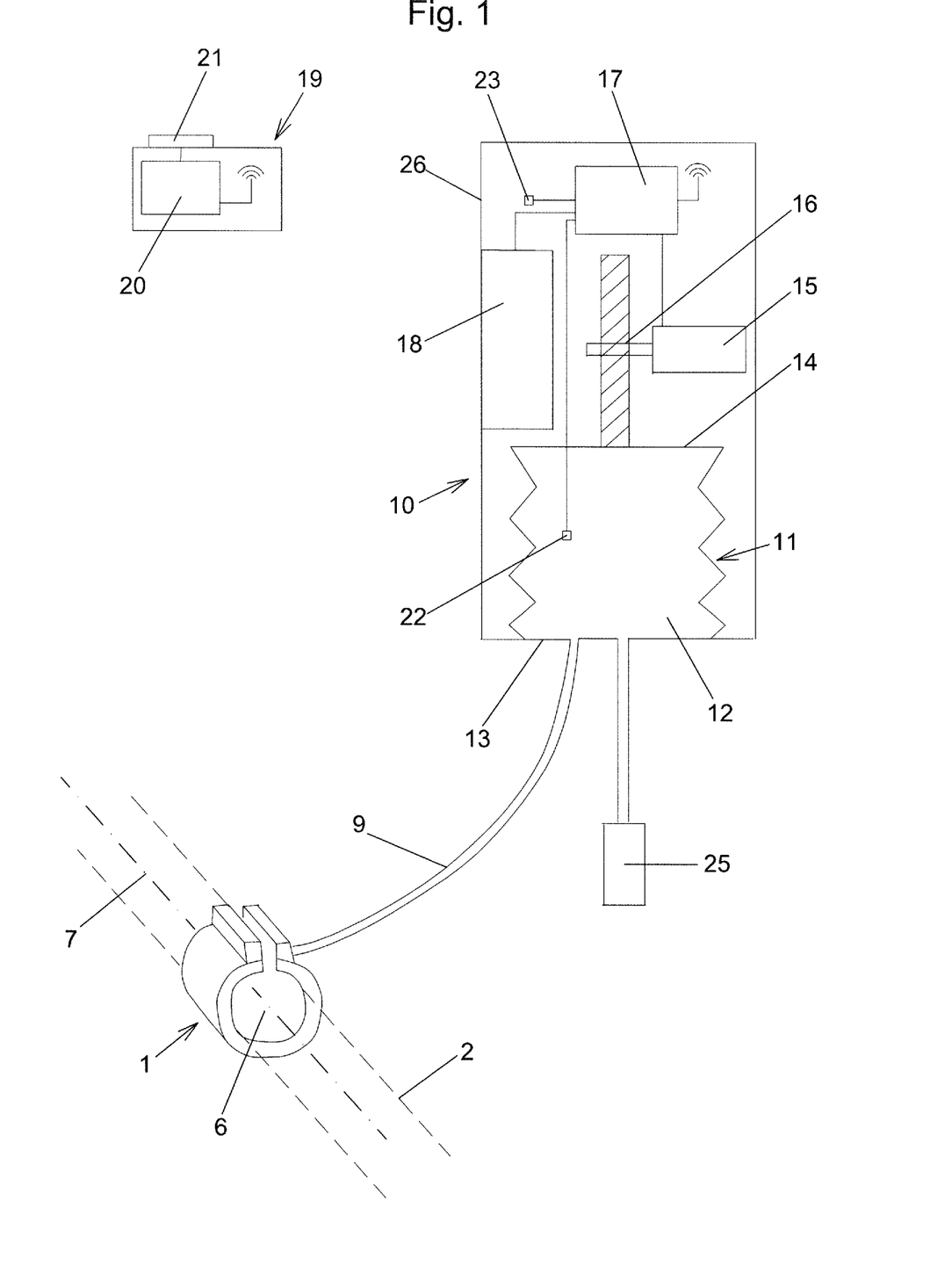
FIG. 1 shows a schematic view of a device configured as an artificial urethral sphincter, in a release state of the band part, in which state the ureter is opened.
Figure 2:
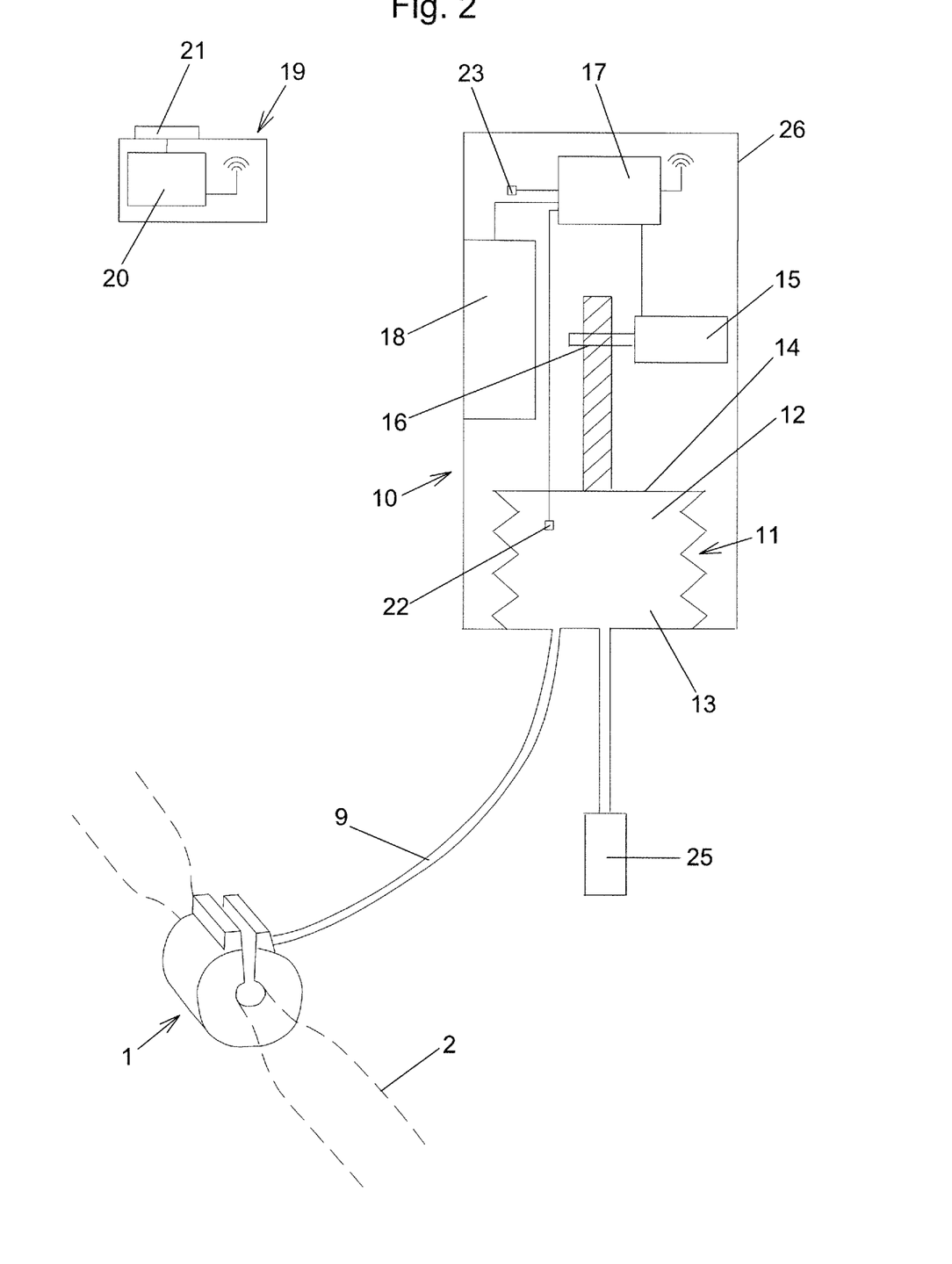
FIG. 2 shows a view analogous to FIG. 1, in a shut-off state of the band part, in which state the ureter is closed.

In the closed state of the band part 1, the latter can thus adopt a release state, in which the anatomical channel is opened (cf. FIG. 1), and a shut-off state, in which the anatomical channel is closed (cf. FIG. 2). In the release state, the pressure of the fluid in the hollow chamber 3 can for example correspond to the atmospheric pressure.

In other embodiments of the invention, the anatomical channel could also just be narrowed to differing extents, without being completely closed. The band part would then adopt different states of narrowing.

Various modifications of the design of the band part are conceivable and possible. For example, it would be possible for special closure parts mounted on the band part 1 to be omitted altogether and for the two ends of the band part to be sewn to each other.

The band part 1 can be made from silicone in a known manner. Other biocompatible materials may also be used in principle.

The band part 1 is connected by a hose 9 to a pump part 11 of a pump unit 10 spatially separate from the band part 1 (cf. FIGS. 1 and 2). By use of the pump unit 10, the amount of fluid in the hollow chamber 3 of the band part 1 can be varied.

In the illustrative embodiment, an attachment stub 8 is integrally formed on one of the closure parts, the interior of which attachment stub 8 is connected to the hollow chamber 3 via a channel running through the closure part. Such an attachment stub could also be provided at another location of the band part. The hose 9 is attached at the attachment stub 8.

The pump part 11 of the pump unit 10 has a receiving space 12 filled with fluid. In the illustrative embodiment, the pump part 11 is formed by a bellows which is closed by a bottom part 13 and a cover part, the latter constituting an actuating element 14. An electric drive 15 acts on the actuating element 14 via a gear 16, for example a worm gear, in order to change the volume of the receiving space 12. The gear 16 is expediently self-locking, such that an adopted position of the actuating element 14 is maintained without supply of electrical energy to the drive 15.

In the illustrative embodiment, the pump part 11 thus forms at the same time a reservoir for the fluid with which the hollow chamber 3 of the band part 1 is filled in order to close the anatomical channel.

For example, the pump part 11 could also be formed by a piston-cylinder unit, in which case the actuating element 14 would be formed by the piston of this piston-cylinder unit.

The pump unit 10 moreover has an electric drive 15 for the pump part 11. The electric drive 15 is controlled by a pump electronics unit 17 of the pump unit 10. The pump electronics unit 17 is supplied with electrical energy from a battery 18 of the pump unit 10, as also is the drive 15. The battery 18 can be in particular a rechargeable battery (accumulator). The charging could in this case take place in a contactless manner by an inductively coupled charger arranged outside the body.

The components of the pump unit 10 are arranged in a housing 26. The housing 26 is made of a biocompatible material or is encased by such a material.

To adjust the band part 1 between the shut-off state and the release state, use is made of an operating unit 19 which is arranged spatially separate from the pump unit 10 and which has at least one operating element 21, for example a key, that can be activated by the user. Further operating elements can be provided. An operating electronics unit 20 of the operating unit 19 in this case communicates with the pump electronics unit 17 via a radio link.

The pump electronics unit 17 and the operating electronics unit 20 together form the electrical control system of the medical device of the invention.

The operating unit 19 can be arranged outside the body. Implantation of the operating unit 19 is conceivable and possible.

A battery (not shown in the figures) serves to supply the operating unit 19 with electrical energy.

A separate operating unit could in principle also be omitted, in which case at least one operating element that can be activated by the user would be arranged at the pump unit. This operating element would have to be able to be activated from outside the body.

Connected to the pump electronics unit 17 is a pressure sensor 22 which, in the illustrative embodiment shown, is located in the fluid-filled receiving space 12 of the pump part 11. Using the pressure sensor 22, the pressure of the fluid in the receiving space 12 can thus be detected, which pressure corresponds to the pressure of the fluid in the hollow chamber 3.

An air pressure sensor 23 is moreover connected to the pump electronics unit 17. By use of this air pressure sensor 23, the electronic control system 17 is able to detect the ambient pressure, which corresponds to the atmospheric pressure. The air pressure sensor 23 could also be arranged in the operating unit 19, and the value detected by it could be transmitted to the pump electronics unit 17 via the radio link. In the illustrative embodiment, a pressure value detected by the pressure sensor 22 and an air pressure value detected by the air pressure sensor 23 are evaluated in the pump electronics unit 17. On the other hand, the pressure value detected by the pressure sensor 22 could be transmitted to the operating electronics unit 20 arranged in the operating unit 19 in order to perform an evaluation therein. If the air pressure sensor 23 is not arranged in the operating unit 19, the air pressure value could also in this case be transmitted from the pump electronics unit 17 to the operating electronics unit 20.

Detected pressure values and air pressure values can be stored either in the pump electronics unit 17 or the operating electronics unit 20.

The first adjustment of the pressure of the fluid in the hollow chamber, in order to close the urethra, can be carried out as follows:

By use of a catheter, water can be allowed to flow through the urethra into the bladder from a container elevated at a defined height (e.g. 50 cm), in which case the pressure of the fluid in the hollow chamber 3 is increased until no more water flows through the urethra. Such a method is known as leak point pressure measurement.

The pressure value thus determined is stored as a reference value for the fluid pressure, at which the anatomical channel is closed. At the same time, the air pressure value corresponding to the atmospheric pressure and detected by the air pressure sensor 23 is stored as a reference value for the atmospheric pressure at which the reference value for the fluid pressure has been determined.

If the anatomical channel has now been closed by applying this reference value for the fluid pressure to the hollow chamber, and if the atmospheric pressure changes with the volume of the fluid remaining constant, then the pressure value output by the pressure sensor 22 also changes by the same quantity.

A change of the volume of the fluid can arise over the course of time, for example through osmosis or as a result of a leak. The fluid volume can also increase through osmosis. Each time before the anatomical channel is opened, the electronic control system checks whether the atmospheric pressure and the fluid pressure have changed in the same way. In other words, that a first difference between the current pressure value and the reference value of the pressure value and a second difference between the current air pressure value and the reference value of the air pressure value are determined by the electronic control system, The first difference and the second difference are compared with each other by the electronic control system. Should the first difference and the second difference deviate from each other, the fluid volume has changed.

If the first difference and the second distance do not deviate from each other, i.e. the first difference and the second difference correspond, the pressure value determined before the anatomical channel is opened is stored as a new reference value for the fluid pressure, and the air pressure value determined before the anatomical channel is opened is stored as a new reference value for the atmospheric pressure. Upon further closure of the anatomical channel, the fluid pressure is adjusted to the new reference value for the fluid pressure (i.e. to the pressure present before the anatomical channel is opened).

However, if a deviation of the first difference from the second difference has arisen, and therefore the fluid volume has changed, i.e. the detected values for the fluid pressure and the atmospheric pressure have not changed to the same degree, then the difference between the change of the atmospheric pressure and the change of the fluid pressure is determined (i.e. the divergence between the first difference and the second difference). The sum of the pressure value determined before the anatomical channel is opened and of the stated difference (divergence between the first difference and the second difference) is stored as a new reference value for the fluid pressure. The atmospheric pressure detected before the anatomical channel is opened is stored as a new reference value for the atmospheric pressure. Upon renewed closure of the anatomical channel, the fluid pressure is adjusted to the new reference value for the fluid pressure. The adjustment of the fluid pressure is effected by the actuating element 14 of the pump part 11, wherein the volume of the receiving space 12 of the pump part 11 becomes correspondingly smaller or larger. This adjustment of the fluid pressure or of the fluid volume could also be designated as a resetting of the fluid pressure.

This process can be repeated each time the anatomical channel is opened. However, the stored reference values could also be retained for a predefined time period, and the described check and, if appropriate, correction could be carried out the next time the anatomical channel is opened only after this predefined time period.

From this deviation of the first difference from the second difference, a certain change of the fluid volume can be inferred. If the fluid volume has changed beyond a predefined extent, i.e. beyond an upper or lower limit value, a warning can be output.

Each opening (freeing) of the anatomical channel can be triggered by the user pressing the operating element 21. A subsequent shutting-off of the anatomical channel can take place automatically after a defined time or can be triggered by the user, for example by further actuation of the operating element 21 or by actuation of another operating element. Various adjustments by the user may be permitted, e.g. an increase of the closing pressure of the fluid for a defined time.

The setup according to the invention also allows the medical device to be controlled in other ways than the one described above. Thus, a reference value for the fluid pressure and a reference value for the air pressure could be stored, and, in each process of closing the anatomical channel, the reference value for the fluid pressure could be adjusted, modified by the difference between the current measured value of the air pressure and the reference value of the air pressure. This procedure is particularly expedient if there is assumed to be a constant volume of the fluid in the system. A measurement of the fluid pressure and of the atmospheric pressure before the anatomical channel is opened could then be omitted or could be carried out for monitoring purposes.

In order to fill the system with fluid, a port 25 is present as customary. This port 25 can be attached to the pump part 11 by a hose, for example.

Instead of the pressure sensor 22 being arranged in the fluid, it is also conceivable and possible to arrange the pressure sensor on a surface 24 of the band part 1 delimiting the through-opening. The pressure exerted on the body tissue is thus measured directly by the pressure sensor. This pressure depends of course on the pressure of the fluid in the hollow chamber 3 and is at least largely proportional thereto. Deviations of the proportionality, as a result of a non-linear behavior of the band part 1 when the hollow chamber 3 increases in size, are preferably below 10%.

Depending on the nature of the drive 15, it could also be possible to use the current consumption of the drive 15 in order to infer the order of magnitude of the fluid pressure. A pressure sensor for detecting the pressure of the fluid could then be omitted.

KEY TO THE REFERENCE NUMBERS

1 band part
1a inner portion
1b rear portion
2 body tissue
3 hollow chamber
4 first closure part
4a insertion opening
5 second closure part
5a tongue
6 through-opening
7 longitudinal center axis
8 attachment stub
9 hose
10 pump unit
11 pump part
12 receiving space
13 bottom part
14 actuating element
15 drive
16 gear
17 pump electronics unit
18 battery
19 operating unit
20 operating electronics unit
21 operating element
22 pressure sensor
23 air pressure sensor
24 surface
25 port
26 housing

The invention claimed is:

1. A medical device for narrowing or shutting off an anatomical channel, the medical device comprising:
a band part which is adapted to be placed around body tissue surrounding the anatomical channel and which is closeable to form a ring that encloses a through-opening for the body tissue, the band part has a hollow chamber, and the through-opening is configured to be made smaller by introducing a fluid into the hollow chamber;
a pump unit that is configured to convey the fluid and includes an electric drive and an electronic control system that controls the electric drive, the electronic control system is configured to detect a pressure value corresponding to or dependent on a pressure of the fluid in the hollow chamber; and
an air pressure sensor configured to detect atmospheric pressure and signal the electronic control system;
wherein the electronic control system is configured to store a reference value of the pressure value detected by the electronic control system and a reference value of an atmospheric air pressure value detected by the air pressure sensor, and the electronic control system is configured to adjust the pressure of the fluid in the hollow chamber for narrowing or shutting off the anatomical channel in dependence on a stored reference value of the pressure value and on the stored reference value of the air pressure value; and
the electronic control system is further configured to determine: a first difference between a current pressure value and the stored reference value of the pressure value and a second difference between a current atmospheric air pressure value and the stored reference value of the air pressure, and a divergence between the first difference and the second difference.

2. The medical device as claimed in claim 1, further comprising a pressure sensor arranged in the fluid or bordering the fluid or on a surface of the band part delimiting the through-opening.

3. The medical device as claimed in claim 1, further comprising an operating unit arranged spatially separate from the pump unit, the pump unit includes a pump electronics unit and the operating unit includes an operating electronics unit, and the electronic control system of the device comprises the pump electronics unit, and wherein the operating electronics unit, and the pump electronics unit and the operating electronics unit communicate via a wireless link.

4. The medical device as claimed in claim 1, wherein the pump unit includes a pump part having a receiving space filled with the fluid, a volume of which is variable by the electric drive.

5. The medical device as claimed in claim 4, wherein the pump part includes a bellows.

6. The medical device as claimed in claim 4, wherein the pump part further comprises an actuating element that is adjustable by the drive, and the volume of the receiving space of the pump part changes upon adjustment of the actuating element.

7. The medical device as claimed in claim 1, wherein the pump unit includes a battery for supplying the drive with electrical energy.

8. The medical device as claimed in claim 1, wherein, in case of a divergence between the first difference and the second difference, the electronic control system is configured to: store a sum of the pressure value determined before the anatomical channel is opened and of the divergence between the first difference and the second difference as a new reference value for the pressure value, and store the atmospheric air pressure value determined before the anatomical channel is opened as a new reference value for the atmospheric air pressure.

9. The medical device as claimed in claim 8, the electronic control system is configured to adjust the pressure of the fluid in the hollow chamber to the new reference value of the pressure value.

10. The medical device as claimed in claim 1, wherein in case of concordance of the first difference and of the second difference, the electronic control system is configured to: store the pressure value determined before the anatomical channel is opened as a new reference value for the pressure value, and store the atmospheric air pressure value detected before the anatomical channel is opened as a new reference value for the atmospheric air pressure value.

11. The medical device as claimed in claim 1, wherein the medical device is an artificial urethral sphincter.

12. A method for monitoring a fluid volume of a medical device that is fillable with a fluid and serves to shut off and free an anatomical channel, the method comprising:
- placing a band part around body tissue surrounding the anatomical channel and closing the band part to form a ring that encloses a through-opening for the body tissue, the band part including a hollow chamber is fillable with fluid in order to make the through-opening smaller, and
- providing a pump unit which serves to convey the fluid and includes an electric drive that is controllable by an electronic control system,
- detecting a pressure value corresponding to or dependent on a pressure of the fluid in the hollow chamber using the electronic control system,
- detecting atmospheric pressure with an air pressure sensor, and outputting an air pressure value to the electronic control system,
- storing a reference value of the pressure value detected by the electronic control system and a reference value of the air pressure value detected by the air pressure sensor in the electronic control system,
- detecting a current pressure value by the electronic control system before the anatomical channel is freed and detecting a current air pressure value by the air pressure sensor, and
- determining a first difference between the current pressure value and the reference value of the pressure value and a second difference between the current air pressure value and the reference value of the air pressure value using the electronic control system, and, determining by comparison of the first difference and the second difference by the electronic control system, a change of the fluid volume.

13. The method as claimed in claim 12, further comprising determining a change of the fluid volume from a deviation of the first difference from the second difference.

14. The method as claimed in claim 13, further comprising outputting a warning if a change of the fluid volume goes beyond at least one of an upper or lower limit value.

* * * * *